United States Patent
Rietveld et al.

(10) Patent No.: US 7,795,028 B2
(45) Date of Patent: Sep. 14, 2010

(54) MODULATING DEVELOPMENTAL TRANSITIONS IN PLANTS

(75) Inventors: Patrice Louis Rietveld, Wageningen (NL); Anne Douwe de Boer, Dreumel (NL)

(73) Assignee: Expressive Research B.V., Wageningen (NL)

( * ) Notice: Subject to any disclaimer, the term of this patent is extended or adjusted under 35 U.S.C. 154(b) by 1543 days.

(21) Appl. No.: 10/466,572

(22) PCT Filed: Jan. 15, 2002

(86) PCT No.: PCT/NL02/00026

§ 371 (c)(1),
(2), (4) Date: Nov. 28, 2003

(87) PCT Pub. No.: WO02/057469

PCT Pub. Date: Jul. 25, 2002

(65) Prior Publication Data

US 2004/0078849 A1    Apr. 22, 2004

(30) Foreign Application Priority Data

Jan. 19, 2001    (EP) ................................ 01200211

(51) Int. Cl.
*C12N 15/29*    (2006.01)
*C12N 15/82*    (2006.01)
*C12N 15/87*    (2006.01)

(52) U.S. Cl. ..................... 435/419; 536/23.1; 536/23.6; 435/320.1

(58) Field of Classification Search ........................ None
See application file for complete search history.

(56) References Cited

OTHER PUBLICATIONS

Stoop-Myer et al (1999, The Plant Journal 20(6):713-717).*
Tori et al (1999, The Journal of Biological Chemistry 274(39):27674-27681).*
Karlowski et al (2003, Plant Molecular Biology 52(1):121-133).*
Torii et al (1999, J. Biol. Chem. 274(39):27674-2768.*
Karlowski et al (2003, Plant Molecular Biology 52(1):121-133).*
Freemont, Paul S., "Ubiquitination: RING for destruction?", *Current Biology* 2000, 10:R84-R87.
Kurup, Smita, et al., "Interactions of the developmental regulator AB13 with proteins identified from developing Arabidopsis seeds", *The Plant Journal* 2000, 21(2):143-155.
Kurup, S., et al., "Interactions of the developmental regulator AB13 with proteins identified from developing Arabidopsis seeds", EMBL 'Online!ACQ9M4B6, Oct. 1, 2000, XP-002172778.
McNellis, Timothy W., et al., "Expression of an N-Terminal Fragment of COP1 Confers a Dominant-Negative Effect on Light-Regulated Seedling Development in Arabidopsis", *The Plant Cell* 1996, 8:1491-1503.
McNellis, Timothy W., et al., "Overexpression of Arabidopsis COP1 Results in Partial Suppression of Light-Mediated Development: Evidence for a Light-Inactivable Repressor of Photomorphogenesis", *The Plant Cell* 1994, 6:1391-1400.
Stoop-Myer, Chatanika, et al., "The N-terminal fragment of Arabidopsis photomorphogenic repressor COP1 maintains partial function and acts in a concentration-dependent manner", *The Plant Journal* 1999, 20(6):713-717.
Tamminen, Iikka, et al., "Ectopic expression of AB13 gene enhances freezing tolerance in response to abscisic acid and low temperature in *Arabidopsis thaliana*", *The Plant Journal* 2001, 25(1):1-8.
Torii, Keiko, U., et al., "The RING Finger Motif of Photomorphogenic Repressor COP1 Specifically Interacts with the RING-H2 Motif of a Novel Arabidopsis Protein", *The Journal of Biological Chemistry* 1999, 274(39):27674-27681.

* cited by examiner

*Primary Examiner*—Stuart F. Baum
(74) *Attorney, Agent, or Firm*—Hoffman & Baron, LLP

(57) ABSTRACT

The invention relates to a method to modulate plant growth or development. The invention provides a method for modulating a developmental transition of a plant comprising modulating expression of a RING-H2 protein or functional fragment thereof in said plant or parts thereof.

9 Claims, 7 Drawing Sheets

Figure 4A:
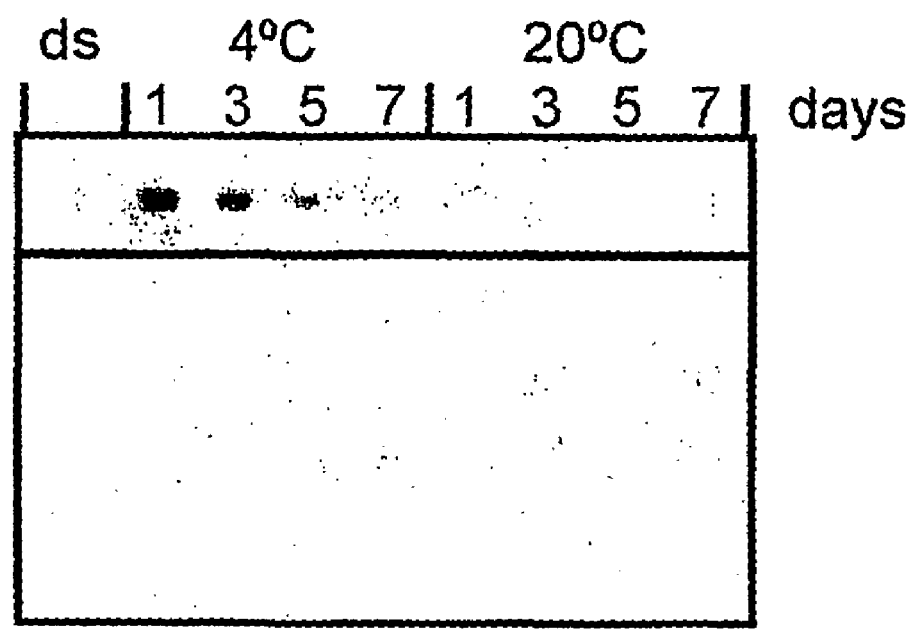
Figure 4B:
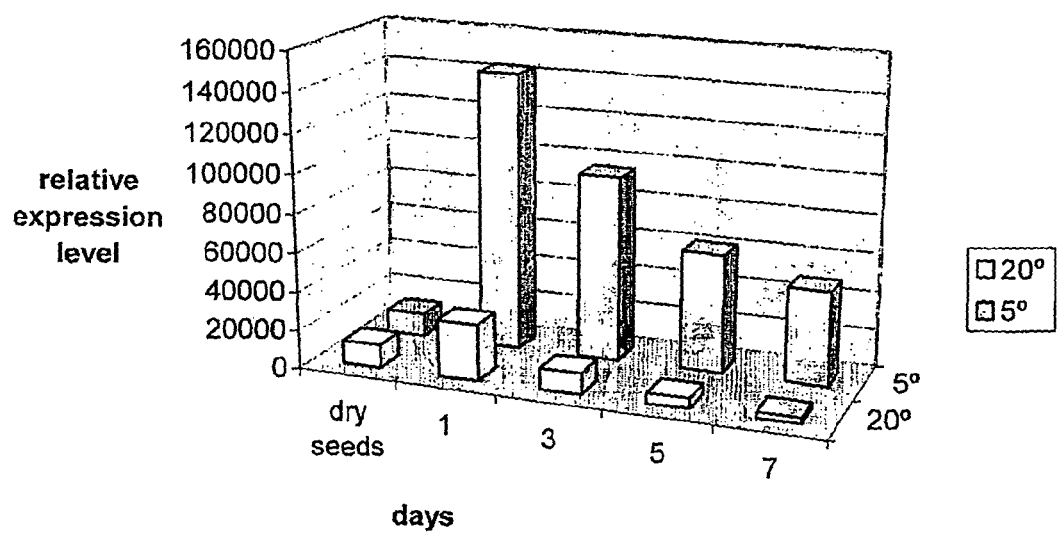
Figure 4C:
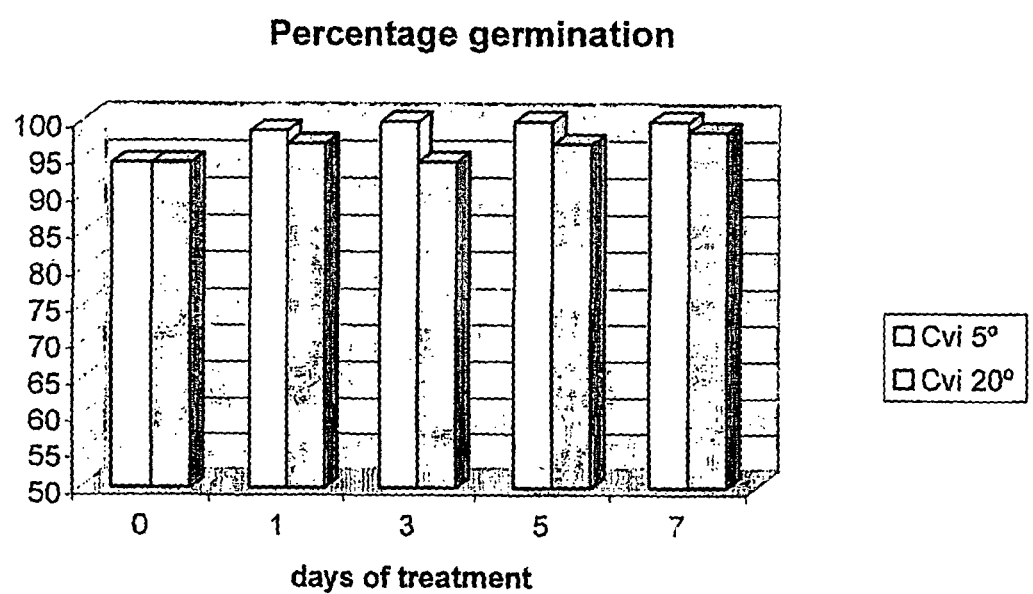

```
                 1                                                           60
TGRING1    (1)   -------MASEAILMEELQALQKKLGKRQSFEEAV AIS LLRD Y TASLALRNSIYSA
OSRING1    (1)   -------MSAPA VEQ LQAL  KLGRKQHFEEAV  LAAAVRDH A ASPALRDLMYST
AIP2       (1)   MDASSSPS SEESLKLEI DLQK L KKLRPEASVQSIHNLLRDHYSSSSFSLRK  YIV
CIP8       (1)   -MSDAPSSS DATASHWCYHCNKRVVV TLDDF VQ E NKGFV SI PTPAAYSSPA P 61                                                          120
TGRING1    (54)  VCRVSTLLQTRYTAPGFWLAGLRLFEDMEKLV VP------SEKVHMK CVSRAREHL E
OSRING1    (54)  VCRVATVLQTRYTAPGFWRAGL LEL  EKLVTNP------SEKE LKTF LRAREHLDE
AIP2       (61)  V RVATVL TRYTA GFWVAGLSLFE AERLVSDA-----SEK HLKSCVA ARE L E
CIP8       (60)  QPLSPDINVE SSIG  FLQMLRI A AP QRSPERHLDVLSY D  FRLEL SR IDD 121                                                         180
TGRING1    (108) MENEL ESN R PDSRYLFEGHLTVGPEPPQPAWLVAQ LLTTYAVAQDLTSM  SS IS-
OSRING1    (108) KENEESM NNRETDT RFLFEGHLTVGPEPP PAWLVAQN------LAREL SILA PSG--
AIP2       (115) VDN PTES QG-----YLFEGHLTV RPPP QWLVQQN------LMS-  ASIVG--
CIP8       (120) DE ED D   EEE---DEBE LTV DEED EDDLRR N------RFPLT TQSRT GRN 181                                                         240
TGRING1    (167) ------EDCNNI GV IISDLRESVHDII NM EMG TEDLENA EASLQEIGAGPQ---K
OSRING1    (160) ------EQCANNNGESR EEMA AAAIMNFLNTMTVDGDLEAALEE SLQ VMA P----K
AIP2       (159) ---------GE SNG-------PTENTIG TANLMQELI GLDMIP TLDDCSPP----R
CIP8       (170) RILDWA ILM I NSI FRMESDRYAGNPA YTDDAA YEALL NLA  DCGGGGRRG 241                                                         300
TGRING1    (218) APPASKEVV NLAVFEVTEEIIAKLGNETECAVCREYLKIT DKAQELPCKHM FHPPCLKP
OSRING1    (210)  PPASKEVVANLPVVTVTEEIIARLGKET CAVC--SLIV DKMQELPCKHL FHPPCLKP
AIP2       (200) APPASKEVVE LPV IFTEELLKK CAE EC ICKENLVIGDKMQELPCKHT FHPPCLKP
CIP8       (230) APPAAK  IEALE FEVS -EGE---MVMVCAVCKDGMVMGE  G  LPCGHCYE GDCIVE 301                                                         352
TGRING1    (278) WLDENNSCPICRHELRTDDH AYEHKK RDREAEEDRKGAA AI ENTEHI--
OSRING1    (268) WLDENNSCPICRHELRTDDHVYEKRRST RAP MLSGVCSS MSEHLNSNRT
AIP2       (260) WLDE NSCPICRHELPTDD KYENWK REKEAEEDRKGA  AVRGGEY YV-
CIP8       (287) WL T NSCEVCR  L TDDAEYEE RKK TMV DSAAASSSSSTSRY----
```

Fig. 1a

Fig. 1b

Fig. 2
A
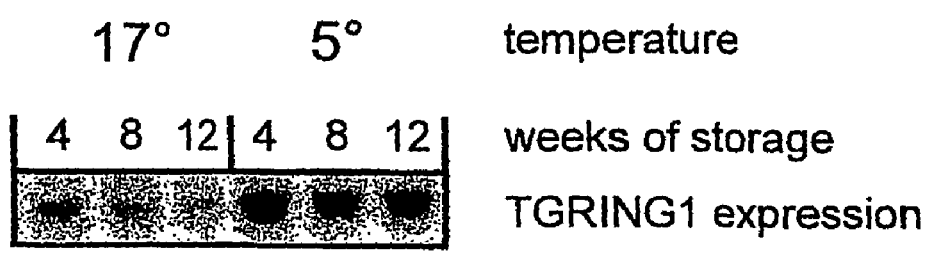
B
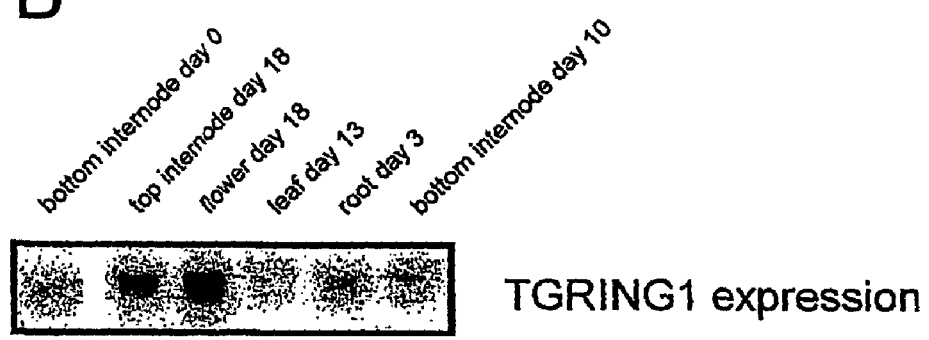

```
   1     GTCGTCGGCTTCCCCTCCGCCAAGAAACAAACCCTCCCACATCTGTTAAATCCAATTCAA

M   A   S   E   A   I
  61     AGACGGTCTGTACAGAGAAGGTGAGTTCGATCTGGATCTGATAATGGCGTCCGAAGCAAT

L   M   E   E   L   Q   A   L   Q   K   K   L   G   K   R   Q   S   F   E   E
 121     CTTGATGGAGGAGCTGCAGGCGCTGCAGAAGAAGCTGGGGAAGAGGCAGTCCTTCGAGGA

A   V   A   A   I   S   S   L   L   R   D   R   Y   P   T   A   S   L   A   L
 181     GGCCGTCGCCGCCATCTCCTCTCTCCTCCGTGACCGCTACCCCACCGCCTCCCTCGCCCT

R   N   S   I   Y   S   A   V   C   R   V   S   T   L   L   Q   T   R   Y   T
 241     CCGCAATTCCATATACTCTGCAGTTTGTCGTGTTTCAACTCTTCTTCAGACAAGATATAC

A   P   G   F   W   L   A   G   L   R   L   F   E   D   M   E   K   L   V   K
 301     GGCACCTGGTTTCTGGCTTGCTGGCTTAAGGCTTTTTGAGGACATGGAGAAACTGGTAAA

V   P   S   E   K   V   H   M   K   K   C   V   S   R   A   R   E   H   L   H
 361     AGTACCTTCAGAAAAAGTCCATATGAAGAAATGTGTTTCCAGGGCTCGCGAGCATCTTCA

E   M   E   N   E   I   P   E   S   N   T   R   Q   P   D   S   R   Y   L   F
 421     TGAAATGGAAAATGAGATCCCTGAATCGAATACTAGACAACCAGATTCTAGGTATCTTTT

E   G   H   L   T   V   G   P   E   P   P   Q   P   A   W   L   V   A   Q   T
 481     TGAGGGCCATTTGACTGTGGGACCTGAACCGCCACAACCTGCATGGCTCGTGGCACAGAC

L   L   T   T   Y   A   V   A   Q   D   L   T   S   M   V   E   S   S   N   S
 541     TCTGCTTACTACTTATGCTGTTGCACAAGATTTGACTTCTATGGTTGAATCTTCTAATTC

E   D   G   N   N   I   D   G   V   A   I   S   D   L   R   E   S   V   H   D
 601     TGAAGATGGTAACAACATAGATGGTGTTGCGATTTCCGATCTTCGCGAGTCTGTTCATGA

L   I   S   N   M   E   E   M   G   G   T   L   D   L   E   N   A   I   E   A
 661     TTTAATAAGCAATATGGAAGAGATGGGCGGAACTTTGGATCTTGAGAATGCCATTGAAGC

S   L   Q   E   I   G   A   G   P   Q   K   A   P   P   A   S   K   E   V   V
 721     GTCATTGCAGGAAATTGGTGCTGGGCCACAGAAAGCACCACCAGCCTCCAAAGAGGTAGT

K   N   L   A   V   F   E   V   T   E   E   I   I   A   K   L   G   N   E   T
 781     TAAAAACCTTGCGGTTTTTGAGGTCACCGAAGAAATTATCGCCAAGTTGGGAAACGAAAC

E   C   A   V   C   R   E   Y   L   K   I   N   D   K   A   Q   E   L   P   C
 841     AGAATGTGCAGTATGCCGTGAGTACTTGAAGATAAATGACAAGGCACAGGAGCTACCTTG

K   H   M   F   H   P   P   C   L   K   P   W   L   D   E   N   N   S   C   P
 901     CAAACATATGTTCCACCCTCCATGTTTGAAGCCGTGGCTGGATGAGAACAACTCTTGCCC

I   C   R   H   E   L   R   T   D   D   H   A   Y   E   H   K   K   E   R   D
 961     GATTTGTAGGCATGAGCTGAGAACAGATGATCATGCGTATGAGCATAAGAAAGAGCGAGA

R   E   A   E   E   D   R   K   G   A   A   N   A   A   D   E   N   T   F   Y
1021     CAGGGAGGCGGAGGAAGATAGGAAGGGAGCGGCAAATGCTGCTGATGAGAATACATTTTA

1081     TATCTGACTGGGATATATGCTGTAAGGCCTCTGATATTGAACACTGTACTATTGTATCCT

1141     TCTGTAATAACAGACTGAATGCGGAATATTTGAATATTTGTCAGCACATTAGAAGCCTTG

1201     CAATGAGCTATTGTGGTTAAAA
```

Fig. 3

SEQUENCE LISTING

<160> NUMBER OF SEQ ID NOS: 17

<210> SEQ ID NO 1
<211> LENGTH: 24
<212> TYPE: DNA
<213> ORGANISM: Artificial Sequence
<220> FEATURE:
<223> OTHER INFORMATION: Synthetic sequence. Description of Artificial
      Sequence: 5' end primer

<400> SEQUENCE: 1
gtcgtcggct tccctccgc caag                                              24

<210> SEQ ID NO 2
<211> LENGTH: 30
<212> TYPE: DNA
<213> ORGANISM: Artificial Sequence
<220> FEATURE:
<223> OTHER INFORMATION: Synthetic sequence. Description of Artificial
      Sequence: 3' end primer

<400> SEQUENCE: 2
tttaaccaca atagctcatt gcaaggcttc                                       30

<210> SEQ ID NO 3
<211> LENGTH: 327
<212> TYPE: PRT
<213> ORGANISM: Tulipa gesneriana

<400> SEQUENCE: 3

Met Ala Ser Glu Ala Ile Leu Met Glu Glu Leu Gln Ala Leu Gln Lys
1               5                   10                  15

Lys Leu Gly Lys Arg Gln Ser Phe Glu Glu Ala Val Ala Ala Ile Ser
            20                  25                  30

Ser Leu Leu Arg Asp Arg Tyr Pro Thr Ala Ser Leu Ala Leu Arg Asn
        35                  40                  45

Ser Ile Tyr Ser Ala Val Cys Arg Val Ser Thr Leu Leu Gln Thr Arg
    50                  55                  60

Tyr Thr Ala Pro Gly Phe Trp Leu Ala Gly Leu Arg Leu Phe Glu Asp
65                  70                  75                  80

Met Glu Lys Leu Val Lys Val Pro Ser Glu Lys Val His Met Lys Lys
            85                  90                  95

Cys Val Ser Arg Ala Arg Glu His Leu His Glu Met Glu Asn Glu Ile
            100                 105                 110

Pro Glu Ser Asn Thr Arg Gln Pro Asp Ser Arg Tyr Leu Phe Glu Gly
        115                 120                 125

His Leu Thr Val Gly Pro Glu Pro Pro Gln Pro Ala Trp Leu Val Ala
    130                 135                 140

Gln Thr Leu Leu Thr Thr Tyr Ala Val Ala Gln Asp Leu Thr Ser Met
145                 150                 155                 160

Val Glu Ser Ser Asn Ser Glu Asp Gly Asn Asn Ile Asp Gly Val Ala
                165                 170                 175

Ile Ser Asp Leu Arg Glu Ser Val His Asp Leu Ile Ser Asn Met Glu
            180                 185                 190

Glu Met Gly Gly Thr Leu Asp Leu Glu Asn Ala Ile Glu Ala Ser Leu
        195                 200                 205

Gln Glu Ile Gly Ala Gly Pro Gln Lys Ala Pro Pro Ala Ser Lys Glu
    210                 215                 220

```
Val Val Lys Asn Leu Ala Val Phe Glu Val Thr Glu Ile Ile Ala
225                 230                 235                 240

Lys Leu Gly Asn Glu Thr Glu Cys Ala Val Cys Arg Glu Tyr Leu Lys
            245                 250                 255

Ile Asn Asp Lys Ala Gln Glu Leu Pro Cys Lys His Met Phe His Pro
            260                 265                 270

Pro Cys Leu Lys Pro Trp Leu Asp Glu Asn Asn Ser Cys Pro Ile Cys
            275                 280                 285

Arg His Glu Leu Arg Thr Asp Asp His Ala Tyr Glu His Lys Lys Glu
            290                 295                 300

Arg Asp Arg Glu Ala Glu Asp Arg Lys Gly Ala Ala Asn Ala Ala
305                 310                 315                 320

Asp Glu Asn Thr Phe Tyr Ile
                325

<210> SEQ ID NO 4
<211> LENGTH: 319
<212> TYPE: PRT
<213> ORGANISM: Oryza sativa

<400> SEQUENCE: 4

Met Ser Ala Pro Ala Ala Val Glu Gln Arg Leu Gln Ala Leu Arg Gln
1               5                   10                  15

Lys Leu Gly Arg Lys Gln His Phe Glu Glu Ala Val Ala Asp Leu Ala
            20                  25                  30

Ala Ala Val Arg Asp His His Ala Ala Ser Pro Ala Leu Arg Asp
            35                  40                  45

Leu Met Tyr Ser Thr Val Cys Arg Val Ala Thr Val Leu Gln Thr Arg
50                  55                  60

Tyr Thr Ala Pro Gly Phe Trp Arg Ala Gly Leu Asn Leu Phe Leu Gly
65                  70                  75                  80

Thr Glu Lys Leu Val Thr Asn Pro Ser Glu Lys Glu Gln Leu Lys Thr
            85                  90                  95

Phe Ile Leu Arg Ala Arg Glu His Leu Asp Glu Lys Glu Asn Glu Glu
            100                 105                 110

Ser Met Pro Asn Asn Arg Glu Thr Asp Thr Arg Phe Leu Phe Glu Gly
            115                 120                 125

His Leu Thr Val Gly Pro Glu Pro Pro Pro Ala Trp Leu Val Ala
130                 135                 140

Gln Asn Leu Ala Arg Glu Leu Ser Ile Leu Ala Glu Pro Ser Gly Asp
145                 150                 155                 160

Gln Gly Ala Asn Asn Gly Glu Ser Arg Ala Glu Glu Met Ala Pro
            165                 170                 175

Ala Ala Ala Ile Met Asn Phe Leu Asn Thr Met Thr Val Asp Gly Asp
            180                 185                 190

Leu Glu Ala Ala Leu Glu Glu Ser Leu Gln Asn Val Met Ala Asn Pro
            195                 200                 205

Lys Val Pro Pro Ala Ser Lys Glu Val Val Ala Asn Leu Pro Val Val
            210                 215                 220

Thr Val Thr Glu Glu Ile Ile Ala Arg Leu Gly Lys Glu Thr Gln Cys
225                 230                 235                 240

Ala Val Cys Ser Leu Leu Val Asp Asp Lys Met Gln Glu Leu Pro Cys
            245                 250                 255

Lys His Leu Phe His Pro Pro Cys Leu Lys Pro Trp Leu Asp Glu Asn
```

```
                    260                 265                 270
Asn Ser Cys Pro Ile Cys Arg His Glu Leu Arg Thr Asp Asp His Val
            275                 280                 285
Tyr Glu Lys Arg Arg Lys Thr Gly Arg Ala Pro Arg Met Leu Ser Gly
        290                 295                 300
Val Gly Ser Ser Cys Met Ser Glu His Leu Asn Phe Asn Arg Thr
305                 310                 315

<210> SEQ ID NO 5
<211> LENGTH: 310
<212> TYPE: PRT
<213> ORGANISM: Arabidopsis thaliana

<400> SEQUENCE: 5

Met Asp Ala Ser Ser Pro Ser Pro Ser Glu Glu Ser Leu Lys Leu
1               5                   10                  15

Glu Leu Asp Asp Leu Gln Lys Gln Leu Asn Lys Lys Leu Arg Phe Glu
            20                  25                  30

Ala Ser Val Cys Ser Ile His Asn Leu Leu Arg Asp His Tyr Ser Ser
        35                  40                  45

Ser Ser Pro Ser Leu Arg Lys Gln Phe Tyr Ile Val Val Ser Arg Val
    50                  55                  60

Ala Thr Val Leu Lys Thr Arg Tyr Thr Ala Thr Gly Phe Trp Val Ala
65                  70                  75                  80

Gly Leu Ser Leu Phe Glu Glu Ala Glu Arg Leu Val Ser Asp Ala Ser
                85                  90                  95

Glu Lys Lys His Leu Lys Ser Cys Val Ala Gln Ala Lys Glu Gln Leu
            100                 105                 110

Ser Glu Val Asp Asn Gln Pro Thr Glu Ser Ser Gln Gly Tyr Leu Phe
        115                 120                 125

Glu Gly His Leu Thr Val Asp Arg Glu Pro Pro Gln Pro Gln Trp Leu
    130                 135                 140

Val Gln Gln Asn Leu Met Ser Ala Phe Ala Ser Ile Val Gly Gly Glu
145                 150                 155                 160

Ser Ser Asn Gly Pro Thr Glu Asn Thr Ile Gly Glu Thr Ala Asn Leu
                165                 170                 175

Met Gln Glu Leu Ile Asn Gly Leu Asp Met Ile Ile Pro Asp Ile Leu
            180                 185                 190

Asp Asp Gly Gly Pro Pro Arg Ala Pro Pro Ala Ser Lys Glu Val Val
        195                 200                 205

Glu Lys Leu Pro Val Ile Ile Phe Thr Glu Glu Leu Leu Lys Lys Phe
    210                 215                 220

Gly Ala Glu Ala Glu Cys Cys Ile Cys Lys Glu Asn Leu Val Ile Gly
225                 230                 235                 240

Asp Lys Met Gln Glu Leu Pro Cys Lys His Thr Phe His Pro Pro Cys
                245                 250                 255

Leu Lys Pro Trp Leu Asp Glu His Asn Ser Cys Pro Ile Cys Arg His
            260                 265                 270

Glu Leu Pro Thr Asp Asp Gln Lys Tyr Glu Asn Trp Lys Glu Arg Glu
        275                 280                 285

Lys Glu Ala Glu Glu Glu Arg Lys Gly Ala Glu Asn Ala Val Arg Gly
    290                 295                 300

Gly Glu Tyr Met Tyr Val
305                 310
```

<210> SEQ ID NO 6
<211> LENGTH: 334
<212> TYPE: PRT
<213> ORGANISM: Arabidopsis thaliana

<400> SEQUENCE: 6

```
Met Ser Asp Ala Pro Ser Ser Pro Asp Ala Thr Ala Ser His Trp
1               5                   10                  15

Cys Tyr His Cys Asn Lys Arg Val Val Glu Thr Leu Asp Asp Phe
                20                  25                  30

Val Val Cys Cys Glu Cys Asn Lys Gly Phe Val Glu Ser Ile Gln Pro
            35                  40                  45

Thr Pro Ala Ala Tyr Ser Ser Pro Ala Pro Gln Pro Leu Ser Pro
        50                  55                  60

Asp Leu Asn Val Glu Asp Ser Ser Ile Gly Ser His Phe Leu Gln Met
65                  70                  75                  80

Leu Arg Leu Leu Ala His Ala Pro Ser Gln Arg Ser Pro Pro Arg His
                85                  90                  95

Leu Asp Val Leu Ser Tyr Glu Asp Asp Phe Phe Arg Leu Glu Leu Asn
                100                 105                 110

Ser Arg Asn Glu Ile Asp Asp Asp Glu Asp Glu Asp Asp Gly
                115                 120                 125

Asp Glu Glu Glu Glu Asp Glu Glu Asn Leu Thr Val Asn Asp Glu
130                 135                 140

Glu Asp Glu Glu Asp Asp Leu Arg Arg Arg Asn Arg Phe Pro Leu Thr
145                 150                 155                 160

Thr Thr Gln Ser Arg Thr Gly Arg Asn Arg Ile Leu Asp Trp Ala Glu
                165                 170                 175

Ile Leu Met Gly Ile Glu Asp Asn Ser Ile Glu Phe Arg Met Glu Ser
                180                 185                 190

Asp Arg Tyr Ala Gly Asn Pro Ala Asp Tyr Ile Asp Ala Ala Gly
                195                 200                 205

Tyr Glu Ala Leu Leu Gln Asn Leu Ala Glu Gly Asp Gly Gly Gly
210                 215                 220

Gly Gly Arg Arg Gly Ala Pro Pro Ala Ala Lys Ser Ala Ile Glu Ala
225                 230                 235                 240

Leu Glu Thr Phe Glu Val Ser Ser Glu Gly Met Val Met Val
                245                 250                 255

Cys Ala Val Cys Lys Asp Gly Met Val Met Gly Glu Thr Gly Lys Lys
                260                 265                 270

Leu Pro Cys Gly His Cys Tyr His Gly Asp Cys Ile Val Pro Trp Leu
                275                 280                 285

Gly Thr Arg Asn Ser Cys Pro Val Cys Arg Phe Gln Leu Glu Thr Asp
                290                 295                 300

Asp Ala Glu Tyr Glu Glu Arg Lys Lys Arg Thr Ser Thr Val Ser
305                 310                 315                 320

Asp Ser Ala Ala Ala Ser Ser Ser Ser Thr Ser Arg Tyr
                325                 330
```

<210> SEQ ID NO 7
<211> LENGTH: 70
<212> TYPE: PRT
<213> ORGANISM: Tulipa gesneriana

<400> SEQUENCE: 7

```
Pro Pro Ala Ser Lys Glu Val Lys Asn Leu Ala Val Phe Glu Val
1               5                   10                  15

Thr Glu Glu Ile Ile Ala Lys Leu Gly Asn Glu Thr Glu Cys Ala Val
                20                  25                  30

Cys Arg Glu Tyr Leu Lys Ile Asn Asp Lys Ala Gln Glu Leu Pro Cys
                35                  40                  45

Lys His Met Phe His Pro Pro Cys Leu Lys Pro Trp Leu Asp Glu Asn
                50                  55                  60

Asn Ser Cys Pro Ile Cys
65                  70

<210> SEQ ID NO 8
<211> LENGTH: 69
<212> TYPE: PRT
<213> ORGANISM: Mus musculus

<400> SEQUENCE: 8

Pro Pro Ala Ser Lys Glu Ser Ile Asp Ala Leu Pro Glu Ile Leu Val
1               5                   10                  15

Thr Glu Asp His Gly Ala Val Gly Gln Glu Met Cys Cys Pro Ile Cys
                20                  25                  30

Cys Ser Glu Tyr Val Lys Gly Glu Val Ala Thr Glu Leu Pro Cys His
                35                  40                  45

His Tyr Phe His Lys Pro Cys Val Ser Ile Trp Leu Gln Lys Ser Gly
                50                  55                  60

Thr Cys Pro Val Cys
65

<210> SEQ ID NO 9
<211> LENGTH: 69
<212> TYPE: PRT
<213> ORGANISM: Rattus rattus

<400> SEQUENCE: 9

Pro Pro Ala Ser Lys Glu Ser Ile Asp Gly Leu Pro Glu Thr Leu Val
1               5                   10                  15

Leu Glu Asp His Thr Ala Ile Gly Gln Glu Gln Cys Cys Pro Ile Cys
                20                  25                  30

Cys Ser Glu Tyr Ile Lys Asp Asp Ile Ala Thr Glu Leu Pro Cys His
                35                  40                  45

His Phe Phe His Lys Pro Cys Val Ser Ile Trp Leu Gln Lys Ser Gly
                50                  55                  60

Thr Cys Pro Val Cys
65

<210> SEQ ID NO 10
<211> LENGTH: 69
<212> TYPE: PRT
<213> ORGANISM: Arabidopsis thaliana

<400> SEQUENCE: 10

Pro Pro Ala Ser Lys Ser Ala Ile Glu Ala Leu Pro Leu Ile Glu Ile
1               5                   10                  15

Asp Pro Thr His Leu Leu Ser Asp Ser Gln Ser His Cys Ala Val Cys
                20                  25                  30

Lys Glu Asn Phe Val Leu Lys Ser Ser Ala Arg Glu Met Pro Cys Asn
                35                  40                  45

His Ile Tyr His Pro Asp Cys Ile Leu Pro Trp Leu Ala Ile Arg Asn
```

```
                    50                  55                  60
Ser Cys Pro Val Cys
 65

<210> SEQ ID NO 11
<211> LENGTH: 66
<212> TYPE: PRT
<213> ORGANISM: Oryza sativa

<400> SEQUENCE: 11

Leu Pro Ala Lys Lys Glu Ala Val Glu Ser Met Pro Thr Val Glu Val
 1               5                  10                  15

Ala Ala Gly Gly Asp Cys Asp Ser Ala Cys Ala Val Cys Leu Glu Asp
                20                  25                  30

Tyr Ala Ala Gly Glu Arg Ala Thr Glu Met Pro Cys Arg His Arg Phe
            35                  40                  45

His Ala Lys Cys Ile Val Pro Trp Leu Lys Met His Ser Ser Cys Pro
        50                  55                  60

Val Cys
 65

<210> SEQ ID NO 12
<211> LENGTH: 67
<212> TYPE: PRT
<213> ORGANISM: Homo sapiens

<400> SEQUENCE: 12

Pro Pro Ala Asp Lys Glu Lys Ile Gln Ala Leu Pro Thr Val Pro Val
 1               5                  10                  15

Thr Glu Glu His Val Gly Ser Gly Leu Glu Cys Pro Val Cys Lys Asp
                20                  25                  30

Asp Tyr Ala Leu Gly Glu Arg Val Arg Gln Leu Pro Cys Asn His Leu
            35                  40                  45

Phe His Asp Gly Cys Ile Val Pro Trp Leu Glu Gln His Asp Ser Cys
        50                  55                  60

Pro Val Cys
 65

<210> SEQ ID NO 13
<211> LENGTH: 70
<212> TYPE: PRT
<213> ORGANISM: Human herpesvirus

<400> SEQUENCE: 13

Ser Pro Thr Pro Ala Asp Ala Gln Gly Ser Cys Gly Gly Gly Pro Val
 1               5                  10                  15

Gly Glu Glu Glu Ala Glu Ala Gly Gly Gly Asp Val Cys Ala Val
                20                  25                  30

Cys Thr Asp Glu Ile Ala Pro Pro Leu Arg Cys Gln Ser Phe Pro Cys
            35                  40                  45

Leu His Pro Phe Cys Ile Pro Cys Met Lys Thr Trp Ile Pro Leu Arg
        50                  55                  60

Asn Thr Cys Pro Leu Cys
 65                  70

<210> SEQ ID NO 14
<211> LENGTH: 1222
<212> TYPE: DNA
<213> ORGANISM: Tulipa gesneriana
```

<400> SEQUENCE: 14

```
gtcgtcggct tcccctccgc caagaaacaa accctcccac atctgttaaa tccaattcaa    60
agacggtctg tacagagaag gtgagttcga tctggatctg ataatggcgt ccgaagcaat   120
cttgatggag gagctgcagg cgctgcagaa gaagctgggg aagaggcagt ccttcgagga   180
ggccgtcgcc gccatctcct ctctcctccg tgaccgctac cccaccgcct ccctcgccct   240
ccgcaattcc atatactctg cagtttgtcg tgtttcaact cttcttcaga caagatatac   300
ggcacctggt ttctggcttg ctggcttaag gcttttgag gacatggaga aactggtaaa   360
agtaccttca gaaaaagtcc atatgaagaa atgtgtttcc agggctcgcg agcatcttca   420
tgaaatggaa aatgagatcc ctgaatcgaa tactagacaa ccagattcta ggtatctttt   480
tgagggccat ttgactgtgg gacctgaacc gccacaacct gcatggctcg tggcacagac   540
tctgcttact acttatgctg ttgcacaaga tttgacttct atggttgaat cttctaattc   600
tgaagatggt aacaacatag atggtgttgc gatttccgat cttcgcgagt ctgttcatga   660
tttaataagc aatatggaag agatgggcgg aactttggat cttgagaatg ccattgaagc   720
gtcattgcag gaaattggtg ctgggccaca gaaagcacca ccagcctcca agaggtagt   780
taaaaacctt gcggttttg aggtcaccga agaaattatc gccaagttgg aaacgaaac   840
agaatgtgca gtatgccgtg agtacttgaa gataaatgac aaggcacagg agctaccttg   900
caaacatatg ttccaccctc catgtttgaa gccgtggctg gatgagaaca actcttgccc   960
gatttgtagg catgagctga gaacagatga tcatgcgtat gagcataaga aagagcgaga  1020
cagggaggcg gaggaagata ggaagggagc ggcaaatgct gctgatgaga atacatttta  1080
tatctgactg ggatatatgc tgtaaggcct ctgatattga acactgtact attgtatcct  1140
tctgtaataa cagactgaat gcggaatatt tgaatatttg tcagcacatt agaagccttg  1200
caatgagcta ttgtggttaa aa                                            1222
```

<210> SEQ ID NO 15
<211> LENGTH: 326
<212> TYPE: PRT
<213> ORGANISM: Tulipa gesneriana

<400> SEQUENCE: 15

```
Met Ala Ser Glu Ala Ile Leu Met Glu Glu Leu Gln Ala Leu Gln Lys
  1               5                  10                  15

Lys Leu Gly Lys Arg Gln Ser Phe Glu Glu Ala Val Ala Ala Ile Ser
             20                  25                  30

Ser Leu Leu Arg Asp Arg Tyr Pro Thr Ala Ser Leu Ala Leu Arg Asn
         35                  40                  45

Ser Ile Tyr Ser Ala Val Cys Arg Val Ser Thr Leu Leu Gln Thr Arg
     50                  55                  60

Tyr Thr Ala Pro Gly Phe Trp Leu Ala Gly Leu Arg Leu Phe Glu Asp
 65                  70                  75                  80

Met Glu Lys Leu Val Lys Val Pro Ser Glu Lys Val His Met Lys Lys
                 85                  90                  95

Cys Val Ser Arg Ala Arg Glu His Leu His Glu Met Glu Asn Glu Ile
            100                 105                 110

Pro Glu Ser Asn Thr Arg Gln Pro Asp Ser Arg Tyr Leu Phe Glu Gly
        115                 120                 125

His Leu Thr Val Gly Pro Glu Pro Pro Gln Pro Ala Trp Leu Val Ala
    130                 135                 140
```

```
Gln Thr Leu Leu Thr Thr Tyr Ala Val Ala Gln Asp Leu Thr Ser Met
145                 150                 155                 160

Val Glu Ser Ser Asn Ser Glu Asp Gly Asn Asn Ile Asp Gly Val Ala
                165                 170                 175

Ile Ser Asp Leu Arg Glu Ser Val His Asp Leu Ile Ser Asn Met Glu
            180                 185                 190

Glu Met Gly Gly Thr Leu Asp Leu Glu Asn Ala Ile Glu Ala Ser Leu
        195                 200                 205

Gln Glu Ile Gly Ala Gly Pro Gln Lys Ala Pro Pro Ala Ser Lys Glu
    210                 215                 220

Val Val Lys Asn Leu Ala Val Phe Glu Val Thr Glu Glu Ile Ile Ala
225                 230                 235                 240

Lys Leu Gly Asn Glu Thr Glu Cys Ala Val Cys Arg Glu Tyr Leu Lys
                245                 250                 255

Ile Asn Asp Lys Ala Gln Glu Leu Pro Cys Lys His Met Phe His Pro
            260                 265                 270

Pro Cys Leu Lys Pro Trp Leu Asp Glu Asn Asn Ser Cys Pro Ile Cys
        275                 280                 285

Arg His Glu Leu Arg Thr Asp Asp His Ala Tyr Glu His Lys Lys Glu
    290                 295                 300

Arg Asp Arg Glu Ala Glu Asp Arg Lys Gly Ala Ala Asn Ala Ala
305                 310                 315                 320

Asp Glu Asn Thr Phe Tyr
                325

<210> SEQ ID NO 16
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa is any amino acid.
<220> FEATURE:
<221> NAME/KEY: MISC_FEATURE
<222> LOCATION: (5)..(13)
<223> OTHER INFORMATION: Xaa is any amino acid.
<220> FEATURE:
<221> NAME/KEY: MISC_FEATURE
<222> LOCATION: (14)..(43)
<223> OTHER INFORMATION: Xaa is any amino acid or may be absent.
<220> FEATURE:
<221> NAME/KEY: MISC_FEATURE
<222> LOCATION: (45)..(45)
<223> OTHER INFORMATION: Xaa is any amino acid.
<220> FEATURE:
<221> NAME/KEY: MISC_FEATURE
<222> LOCATION: (46)..(47)
<223> OTHER INFORMATION: Xaa is any amino acid or may be absent.
<220> FEATURE:
<221> NAME/KEY: MISC_FEATURE
<222> LOCATION: (49)..(50)
<223> OTHER INFORMATION: Xaa is any amino acid.
<220> FEATURE:
<221> NAME/KEY: MISC_FEATURE
<222> LOCATION: (51)..(51)
<223> OTHER INFORMATION: Xaa is any amino acid or may be absent.
<220> FEATURE:
<221> NAME/KEY: MISC_FEATURE
<222> LOCATION: (53)..(54)
<223> OTHER INFORMATION: Xaa is any amino acid.
<220> FEATURE:
<221> NAME/KEY: MISC_FEATURE
<222> LOCATION: (56)..(59)
```

```
<223> OTHER INFORMATION: Xaa is any amino acid.
<220> FEATURE:
<221> NAME/KEY: MISC_FEATURE
<222> LOCATION: (60)..(103)
<223> OTHER INFORMATION: Xaa is any amino acid or may be absent.
<220> FEATURE:
<221> NAME/KEY: MISC_FEATURE
<222> LOCATION: (105)..(106)
<223> OTHER INFORMATION: Xaa is any amino acid.

<400> SEQUENCE: 16

Cys Xaa Xaa Cys Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Cys Xaa Xaa Xaa His
            35                  40                  45

Xaa Xaa Xaa Cys Xaa Xaa Cys Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Cys Xaa Xaa Cys
                100                 105

<210> SEQ ID NO 17
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa may be any amino acid.
<220> FEATURE:
<221> NAME/KEY: MISC_FEATURE
<222> LOCATION: (5)..(13)
<223> OTHER INFORMATION: Xaa may be any amino acid.
<220> FEATURE:
<221> NAME/KEY: MISC_FEATURE
<222> LOCATION: (14)..(43)
<223> OTHER INFORMATION: Xaa may be any amino acid or may be absent.
<220> FEATURE:
<221> NAME/KEY: MISC_FEATURE
<222> LOCATION: (45)..(45)
<223> OTHER INFORMATION: Xaa may be any amino acid.
<220> FEATURE:
<221> NAME/KEY: MISC_FEATURE
<222> LOCATION: (45)..(45)
<223> OTHER INFORMATION: Xaa may be any amino acid.
<220> FEATURE:
<221> NAME/KEY: MISC_FEATURE
<222> LOCATION: (46)..(47)
<223> OTHER INFORMATION: Xaa may be any amino acid or may be absent.
<220> FEATURE:
<221> NAME/KEY: MISC_FEATURE
<222> LOCATION: (49)..(50)
<223> OTHER INFORMATION: Xaa may be any amino acid.
<220> FEATURE:
<221> NAME/KEY: MISC_FEATURE
<222> LOCATION: (51)..(51)
<223> OTHER INFORMATION: Xaa may be any amino acid or may be absent.
<220> FEATURE:
<221> NAME/KEY: MISC_FEATURE
<222> LOCATION: (53)..(54)
<223> OTHER INFORMATION: Xaa may be any amino acid.
<220> FEATURE:
<221> NAME/KEY: MISC_FEATURE
<222> LOCATION: (56)..(59)
```

-continued

```
<223> OTHER INFORMATION: Xaa may be any amino acid.
<220> FEATURE:
<221> NAME/KEY: MISC_FEATURE
<222> LOCATION: (56)..(59)
<223> OTHER INFORMATION: Xaa may be any amino acid.
<220> FEATURE:
<221> NAME/KEY: MISC_FEATURE
<222> LOCATION: (60)..(103)
<223> OTHER INFORMATION: Xaa may be any amino acid or may be absent.
<220> FEATURE:
<221> NAME/KEY: MISC_FEATURE
<222> LOCATION: (105)..(106)
<223> OTHER INFORMATION: Xaa may be any amino acid.

<400> SEQUENCE: 17

Cys Xaa Xaa Cys Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Cys Xaa Xaa Xaa His
        35                  40                  45

Xaa Xaa Xaa His Xaa Xaa Cys Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Cys Xaa Xaa Cys
            100                 105
```

MODULATING DEVELOPMENTAL TRANSITIONS IN PLANTS

This application is the U.S. National Phase of International Application Number PCT/NL02/00026 filed on 15 Jan. 2002, which is incorporated herein by reference.

BACKGROUND OF THE INVENTION

The invention relates to a method to modulate plant growth or development.

Apart from short-term environmental factors, such as the daily rhythm of night and day and the immediate availability of water and nutrients, long-term environmental factors, such as periods with low temperature, (lack of) humidity, or little day length, have an important role in the life cycle of many plants. Where a short-term environmental factor such as ambient light has an immediate effect on day-to-day morphogenesis (e.g. seedlings grown in the light are characterised by short hypocotyls and expanded green cotyledons and seedlings grown in darkness are etiolated, with elongated hypocotyls and closed cotyledons) long-term environmental factors often determine or have effect on the transition of a plant from one phase to another phase in its development, and in particular effect plants that are in a developmental pause in their development.

For example, periods with low temperatures occurring in the temperate climate zone during winters effect many transitional aspects of plants. Typical transitional events are stem elongation (bolting) and the onset of flowering and the formation of fruit (fruiting), another is the event that is seen as the break-through event of dormant seed, germination.

Some plant species need a developmental pause comprising a prolonged period of low temperature and/or little light or day length to induce flowering, and, in a process called vernalisation, for many plants traditionally artificial methods (such as forcing) are in widespread use to provide for the premature bolting, flowering and/or fruiting, or germination of a plant, seed, seedling or bulb to obtain commercially attractive plants or plant parts (seedlings, flowers or flowering plants, fruit) in a season in which otherwise such a product would nor or not natively be available.

In some species flowering and stem elongation may be induced at the same time. Other species need a period of low temperature to induce the elongation of the stem, a process that we will further refer to as bolting. In these species the process of flower induction and formation precedes the required period of low temperature, so the two processes are temporally separated. Yet other processes influenced by long-term environmental factors (e.g. low temperatures or dryness) are quiescence, dormancy and germination of seeds. These long-term environmental factors or processes often synchronise a plant's development to the seasons and/or climatic conditions of the place of growth, and reflect evolutionary adaptations to various conditions under which a particular plant or species grows.

Tulip is an example of a species used as a model to study these various aspects of long-term environmentally induced changes in plant growth, via the study of the process of bolting [4]. Another process where low temperature is often involved is seed dormancy. Low temperature induced stem elongation can be viewed as a form of dormancy breaking, and stratification, vernalisation and dormancy breaking in tree buds are similar processes driven by low temperature. In germination of dormant seed in Arabidopsis, besides the chilling requirement to overcome dormancy, other similarities between bolting of tulips and the germination of the dormant seed are the fact that all organs are formed within a protective structure to enable rapid growth after dormancy has been removed, reserve substances are stored in specialised leaf like organs (for example in the form of starch in the cotyledons of Arabidopsis, and also in the form of starch in the bulb scales of tulip), and during dormancy there is a low water potential [5].

SUMMARY OF THE INVENTION

The invention provides a method to modulate a developmental transition of a plant, thereby for example providing a break-through in a developmental pause, said method essentially independent of a long-term environmental factor as discussed above, thereby providing a method to modulate transition of a plant from one developmental phase to another. In particular, a method for modulating developmental transitions in plants is provided wherein said transition comprises germination, bolting, the onset of flowering or fruiting. Herein we present the isolation of a low temperature induced expression product of a plant RING finger, subclass RING-H2 protein from Tulip with homology to other plant (such as Arabidopsis) proteins that interacts with developmental regulators. The implications of this are expression of said plant RING finger or RING-H2 protein, as shown herein for the low temperature induced TGRING1 expression, targets a plant's homologue of ABI3 for proteolysis, and thereby ends a developmental pause, e.g. the state of dormancy or quiescence, allowing the plant to break-through (for example transcend) from one developmental phase to another and grow towards its subsequent developmental state. Although the fact that RING or RING-H2 proteins have been recognized as involved in ubiquitination or proteolysis before, the involvement of these proteins in developmental changes in plants has not been demonstrated ear er This is especially true for the developmental changes such as those relating to germination, stratification, bolting, the onset of flowering or fruiting, low temperature induced stem elongation, dormancy breaking, bulb induction, timing of flowering. For example, Stoop-Myer et al [17] show that an N-terminal fragment of COP1 retains part of it's functionality. They indicate this fragment to have at least two functional domains, the RING and coiled-coil domains. But, importantly they don't assign the retained functionality to the RING domain, and neither do they propose a function for this domain alone. Also, McNellis et al [18] show that an N-terminal fragment of COP1 retains part of it's functionality. Again they indicate this fragment to have at least two functional domains, the RING and coiled-coil domains. Again, they don't assign the retained functionality to the RING domain. McNellis et al [19] show by overexpression of COP1 it's role in photomorphogenesis. They indicate COP1 to have at least three functional domains, the RING domain, the coiled-coil domain, and the WD-40 repeat domain. But, importantly they don't assign the functionality of COP1 to the RING domain, and neither do they propose a function for this domain alone. Kurup et al [16] show in their article that AIP2 has an interaction with the arabidopsis developmental regulator ABI3. They fail to recognize the role of AIP2 and other RING-H2 proteins in developmental transitions, on the contrary, they propose a role for AIP2 as a transcriptional activator. The article by Freemont [20] is the first published article that proposes a general role for RING and RING-H2 domains in ubiquitination and proteolytic targeting. His article focuses mainly on RING proteins found in animal systems with one exception: PRT1 [21]. The arabidopsis PRT1 protein is apparently involved in a particular kind of pathway, the 'N-end rule' ubiquitination pathway.

However, neither in this article nor in the article by Potuschak et al, [21] is there any mention of using RING finger or RING-H2 proteins for manipulating the protein level of developmental regulators in order to obtain a developmental change in plants. Although the fact that RING or RING-H2 proteins have been recognized as involved in ubiquitination or proteolysis before, the involvement of these proteins in developmental changes in plants has not been demonstrated earlier This is especially true for the developmental changes such as those relating to germination, stratification, bolting, the onset of flowering or fruiting, low temperature induced stem elongation, dormancy breaking, bulb induction, timing of flowering. Tamminen [22] illustrates that ectopic expression of ABI3 results in changes in freezing tolerance. The present invention provides the use of RING or RING-H2 proteins for developmental transitions of plants by manipulating the protein level of ABI3 or other developmental regulators by targeting them for proteolysis by ubiquitination. The article by Torii et al [23] shows that the arabidopsis protein CIP8 interacts with the arabidopsis photomorphogenic regulator COP1. The interaction is ascribed to the RING domain of COP1 and the RING-H2 domain of CIP8. However, the article does not indicate or propose a functional role for the RING or RING-H2 domain in ubiquitination or proteolysis. It only proposes a role as a protein-protein interaction domain.

Typical plant proteins having the desired RING finger or RING-H2 motif can be found in FIG. 1A and B, and others may be found by simple alignment as shown herein. In a preferred embodiment the invention provides a method for modulating a developmental transition of a plant comprising modulating expression of a RING finger or RING-H2 protein or functional fragment thereof in said plant or parts thereof, in particular wherein said transition comprises germination, stratification, bolting, the onset of flowering or fruiting. Such a RING finger or RING-H2 protein, as herein is disclosed, provides ubiquination and/or proteolysis of a target protein (e.g. developmental regulatory protein) related to the transition from one developmental phase to another, thereby for example providing for proteasome-mediated degradation and removal of the target protein (e.g. regulatory protein) involved. A target protein as used herein is a protein capable of modulating a developmental transition of a plant. Particular regulatory proteins to be mentioned here comprise for example COP1, HY5, FLC, FRIGIDA and LD. Preferred herein is modulation of a regulatory protein that in Arabidopsis is known as abscisic acid-insensitive3 (ABI3) or a homologue thereof.

The invention provides a method wherein said RING finger or RING-H2 protein or functional fragment thereof is at least functionally equivalent or homologous to a plant RING finger or RING-H2 protein as shown in FIGS. 1A and 1B. A functional fragment of a RING finger protein contains for example the RING finger (C3HC4) motif:

Cx(2)Cx(9,39)Cx(1,3)Hx(2,3)Cx(2)Cx(4,48)Cx(2)C
(SEQ ID. No: 16)

and a functional fragment of a RING-H2 proteins contains for example the RING-H2 (C3H2C3) motif:

Cx(2)Cx(9,39)Cx(1,3)Hx(2,3)Cx(2)Cx(4,48)Cx(2)C
(SEQ. ID. NO: 17)

or a motif functionally equivalent thereto. The above used coding is according to the IUPAC-rules: C stands for cysteine, H stands for histidine and x codes for any amino acid. The numbers between the brackets show the number of repetitions, so for example, x(9,39) means a stretch of 9 to 39 amino acids residues, where each residue can be any amino acid. In TGRING1 this motif comprises amino acids 248-288 of SEQ. ID. NO: 15.

The invention also provides an isolated and/or recombinant nucleic acid encoding a plant RING finger or RING-H2 protein or functional fragment thereof comprising an amino acid sequence that is preferably at least 50%-60% homologous, more preferred 70% homologous and even more preferred 95% homologous to the sequence in FIG. 3, and retains a similar function [i.e. is "essentially equivalent" to the sequence in FIG. 3]. "Essentially equivalent" as used herein means a functional equivalent, e.g. deliberate amino acid substitution may be made on the basis of similarity in polarity, charge, solubility, hydrophobicity, and/or the amphipathetic nature of the residues as long as the biological activity of the polypeptide is retained. Homology is generally over the full-length of the relevant sequence shown herein. As is well-understood, homology at the amino acid level is generally in terms of amino acid similarity or identity. Similarity allows for "conservative variations", i.e. substitution of one hydrophobic residue such as isoleucine, valine, leucine or methionine for another, or the substitution of one polar residue for another, such as arginine for lysine, glutamic for aspartic acid, or glutamine for asparagine. Deliberate amino acid substitution maybe made on the basis of similarity in polarity, charge, solubility, hydrophobicity, and/or the amphipathetic nature of the residues as long as the biological activity of the polypeptide is retained. In a preferred embodiment, all percentage homologies referred to herein refer to percentage sequence identity, e.g. percent (%) amino acid sequence identity with respect to a particular reference sequence can be the percentage of amino acid residues in a candidate sequence that are identical with the amino acid residues in the reference sequence, after aligning the sequences and introducing gaps, if necessary, to achieve the maximum percent sequence identity, without considering any conservative substitutions as part of the sequence identity. Amino acid similarity or identity can be determined by genetic programs known in the art.

The invention provides a method wherein said RING finger or RING-H2 protein act as a ubiquitin-protein ligase (E3) or subunit of such an enzyme. Modification with chains of ubiquitin (Ub) constitutes a primary mechanism by which proteins are targeted for proteasomal degradation. Protein ubiquitination is accomplished through a complex process involving ubiquitin-activating enzymes (E1s), ubiquitin-conjugatingenzymes (E2s) and, in some cases, specificity-conferring ubiquitinligases (E3). The E1 enzyme acts first and passes Ub to an E2 enzyme ready for targeting to a protein substrate (target protein). RING finger or RING-H2 protein, which may act as nucleic acid or protein binding domains may also act as ubiquitin protein ligase (E3) or subunits of such enzymes. Ubiquitin ligases E3 are loosely defined as proteins or protein complexes are responsible for substrate recognition and promoting polyubiquitin ligation to the substrate marking it for degradation by the 26S proteosome. E3 enzymes assemble multiubiquitin chains on a variety of regulatory proteins and thus targets them for proteolysis by the 26S proteosome.

The invention provides a method according to the invention wherein said RING finger or RING-H2 protein may interact at least with a target protein and/or a ubiquitin conjugating enzyme (E2) allowing transfer of ubiquitin residues from said ubiquitin conjugating enzyme to said target protein. E3s may interact with E2s to form thioester linkages with ubiquitin before modifying target proteins. Some E3s do not act as ubiquitin carriers that form thioester intermediates, but instead act as bridges between E2s and target proteins that provide a favorable environment for the transfer of ubiquitin. The RING finger or RING-H2 protein may provide a site of interaction with E2 that allows for the direct transfer of Ub from E2 to target lysines. This reaction results in the formation of an isopeptide bond between the C terminus of ubiquitin and the epsilon amino group of a lysine residue in the protein substrate. Lysine residues within the attached ubiquitin residues can serve as acceptor sites, resulting in the assembly of a multiubiquitin chain, which can to function as a recognition signal for the 26S proteasome.

The RING finger or RING-H2 protein may have other roles in ubiquitination reactions than providing binding sites for E2s. RING finger or RING-H2 protein can instead function as allosteric activators of E2s. The invention further provides a method according to the invention wherein said RING finger or RING-H2 protein act as an allosteric activator of a ubiquitin conjugating enzyme (E2). It is understood that said RING finger or RING-H2 protein acts in pathways other than ubiquitin or in ubiquitin-like pathways, to modulate a developmental transition of a plant.

In particular, the invention provides such a nucleic acid derived from a bulb. A bulb as used herein is a modified underground stem which has one or more buds enclosed in fleshy modified leaves or scales which supply energy to the bud(s) when they start to grow, for example onions and tulips have bulbs. Also, the invention provides a vector comprising a nucleic acid according to the invention, and host cell comprising a nucleic acid or vector according to the invention. An example of such a vector is the plant transformation vector pBIN19, which is often used to deliver a piece of DNA, for example a piece of DNA encoding the TGRING1 protein or functional fragment thereof, to the genome of a plant. The procedure or method for preparing a transformant can be performed according to the conventional technique used in the fields of molecular biology, biotechnology and genetic engineering.

Preferably, such a host cell comprises a plant cell, allowing the generation of a plant or part thereof comprising a nucleic acid according to the invention. 'Plant cell', as used herein, amongst others comprises seeds, suspension cultures, embryos, meristematic regions, callous tissues, protoplasts, leaves, roots, shoots, bulbs, gametophytes, sporophytes, pollen and microspores. The target plant may be selected from any monocotyledonous or dicotyledonous plant species, such as for example ornamental plants, vegetables, arable crops etc. 'Dicotyledons' (and all scientific equivalents referring to the same group of plants) form one of the two divisions of the flowering plants or angiospermae in which the embryo has two or more free or fused cotyledons. 'Monocotyledons' (and all scientific equivalents referring to the same group of plants) form one of the two divisions of the flowering plants or angiospermae in which the embryo has one cotyledon. 'Angiospermae' or flowering plants are seed plants characterized by flowers as specialized organs of plant reproduction and by carpels covering the ovaries. Also included are gymnospermae. Gymnospermae are seed plants characterized by strobili as specialized organs for plant reproduction and by naked sporophylls bearing the male or female reproductive organs, for example woody plants.

'Ornamental' plants are plants that are primarily in cultivation for their habitus, special shape, (flower, foliage or otherwise) colour or other characteristics which contribute to human well being indoor as cut flowers or pot plants or outdoors in the man made landscape, for example bulbous plant species like Tulipa, Freesia, Narcissus, Hyacinthus etc. 'Vegetables' are plants that are purposely selected or bred for human consumption of foliage, tubers, stems, fruits, flowers of parts of them and that may need an intensive cultivation regime. 'Arable crops' are generally purposely bred or selected for human objectivity's (ranging from direct or indirect consumption, feed or industrial applications such as fibers) for example soybean, sunflower, corn, peanut, maize, wheat, cotton, safflower and rapeseed.

In particular, the invention provides use of a nucleic acid or a vector according to the invention in a method for modulating a plant. Preferably, said method comprises modulating a developmental transition of said plant.

Preferably, said modulation is achieved by providing said plant with a nucleic acid encoding a RING finger or RING-H2 protein or functional fragment thereof. The invention is for example considered useful to replace forcing of plants with the purpose to accelerate a transition, for example to obtain early flowering bulbs for sale, but can equally well be applied to delay transition in plants where that may be required.

In a particular embodiment, the invention provides a method, for example useful in in-vitro propagation of bulbs, such as tulip bulbs, comprising transient expression of said nucleic acid encoding a RING finger of RING-H2 protein. Other examples of transitions which can be influenced or modulated (accelerated or delayed) with the described invention comprise germination, stratification, bolting, the onset of flowering, fruiting, flowering timing, low temperature induced stem elongation, dormancy breaking or bulb induction, whereby said nucleic acid can also be transiently expressed. The invention additionally provides a plant (if desired only transiently) provided with a nucleic acid encoding a RING finger or RING-H2 protein or functional fragment thereof.

The invention also provides a method for a determining a stage in a or leading up to a developmental transition of a plant comprising determining expression of a RING finger or RING-H2 gene product (mRNA or protein or functional fragment thereof in said plant or parts thereof, and/or comprising determining ubiquination and/or proteolysis of a target protein which interacts or is affiliated with said RING finger or RING-H2 gene product (mRNA or protein or functional fragment thereof). Such a method is useful in a method for selecting a plant for being at a transition phase of its development comprising determining expression of a RING finger or RING-H2 gene product functional fragment thereof in said plant or parts thereof, for example to determine whether said plant is in or close to a distinct developmental phase such as for example germination, stratification, bolting, the onset of flowering or fruiting.

The invention further provides a method for selecting a plant for being at a transition phase of its development comprising determining expression of a RING finger or RING-H2 gene product or functional fragment thereof and/or comprising determining ubiquination and/or proteolysis of a target protein which interacts or is affiliated with said RING finger or RING-H2 gene product (mRNA or protein or functional fragment thereof. Plants with the desired characteristics are now easily selectable and herein also provided.

The invention also provides a method for obtaining a plant or progeny thereof having a desired quality trait related to developmental transitions comprising determining expression of a RING finger or RING-H2 gene product or functional fragment thereof in said plant or parts thereof, and/or comprising determining ubiquination and/or proteolysis of a target protein which interacts or is affiliated with said RING finger or RING-H2 gene product (mRNA or protein or functional fragment thereof.

It is for example now possible to more easily select or breed plants with a desired developmental transition pattern. For example to obtain tulips or other plants with a reduced cold requirement for flowering, or a plant of which the germination of the seeds is either delayed or accelerated, it is now possible to check the progeny of different crosses for expression levels of a RING finger or RING-H2 mRNA or protein or functional fragment thereof regulating said quality (cold requirement or time of seed germination).

The invention is further explained in the detailed description without limiting the invention thereto.

DETAILED DESCRIPTION

Plant Material and RNA Isolation

Tulip bulbs were harvested in the summer (July) and stored at 20° C. until at least two weeks after stage G (September). All storage treatments were performed in dark ventilated rooms. Bulbs were then either transferred to 5° C. for low temperature treatment, or to 17° C.

For the differential display analysis, after transfer to 5° C. or 17° C., samples were taken after 4, 8 and 12 weeks. The same was done in another year for the Northern blot analysis of differential expression during temperature treatment. For the Northern blot analysis of the different organs after planting, bulbs were transferred to 17° C. in September until the end of December and then transferred to 5° C. for 12 weeks. After planting and growing at 23° C. (12 hr light/12 hr dark), organ samples were taken at the indicated days after planting. All samples were frozen in liquid nitrogen and stored at −80° C. or freeze dried. RNA was isolated using CTAB as described [3]. Northern blots were performed using formaldehyde/agarose gels as described [1]. Hybridization was performed at 68° C. using 50% formamide buffer, and an $\alpha^{32}P$-CTP labeled RNA probe.

Cloning Procedure

Differential display PCR (DDRT-PCR) was performed as described [2]. The differential band was excised, and reamplified using the same conditions as during the DDRT-PCR, except that dNTP concentration was 100 µM. The PCR product was cloned. All cloning of PCR products was in the pGEM-T vector (Promega, Madison USA). After sequencing, two nested 5' RACE (Rapid Amplification of cDNA Ends) reactions were performed using the Marathon kit (ClonTech, Palo Alto USA) with fragment specific primers. The resulting fragment was cloned and sequenced. The total fragment was now reamplified and cloned using new primers from the 5'-end (5'-GTCGTCGGCTTCCCCTCCGCCAAG-3' SEQ. ID. NO: 1) and 3'-end (5'-TTTAACCACAATAGCT-CATTGCAAGGCTTC-3' SEQ. ID. NO: 2) and proofreading enzyme (KlenTaq, ClonTech). Two clones were sequenced on both strands and found to be identical. Requested EST clones were also sequenced on both strands. Sequencing was performed on an automated sequencer (ALFexpress, Amersham Pharmacia Biotech, Uppsala, Sweden), using kits recommended by manufacturer.

Sequence Analysis

Sequences were analyzed using DNASIS (Hitachi Software, Olivet, France) and GeneRunner (Hastings Software Inc, Hastings on Hudson, USA) software packages. Database searches were performed using the NCBI Blast server Multiple alignments were performed at EBI ClustalW server, using standard settings. Alignments were shaded using Boxshade 3.2 (ISREC, Epalinges s/Lausanne, Switzerland).

Results

Cloning and Sequence of TGRING-H2 and Similar EST Sequences

Using differential display a screening was performed for mRNA's expressed at a higher level in the bottom internode of dry stored tulip bulbs at 5° C. compared to those stored at 17° C. A 218 bp fragment was found to be differential and was cloned. Because DDRT-PCR fragments often derive from the non-coding 3'-end, a 5'-RACE reaction was performed. The resulting fragment was sequenced and new 5'- and 3'-primers were designed to reamplify the full-length cDNA using proofreading enzyme.

The resulting 1222 bp clone contains an open reading frame of 327 amino acids with a predicted molecular mass of 36.7 kD. The cDNA is either full length or close to full length because there is an in frame stop codon preceding the predicted start codon. The transcript size was also confirmed on a Northern blot (not shown). The encoded acidic protein (isoelectric point 5.02) has as most significant feature a C-terminal RING-H2 domain, a variant RING-finger domain. It is predicted to be targeted to the cytoplasm. The protein will be further referred to as TGRING1.

Database searches revealed two partially sequenced EST-sequences and one published Arabidopsis sequence, CIP8 [COP-1 Interacting Protein 8; [13]] with significant homology beyond the RING-H2 domain. The EST-clones, rice EST C10402 and arabidopsis EST TAI386, were requested and full length sequenced. Recently, the sequence of the Arabidopsis EST TAI386 sequence has been published as AIP2, an ABI3 interacting protein [8], and will be further referred to as such. The rice EST will be further referred to as OSRING1.

A multiple alignment shows that the two EST sequences are highly homologous to the tulip sequence over the whole length of the protein. OSRING1 shows 58% identity and 72% similarity over 300 amino acids, and AIP2 51% and 64% respectively over 301 amino acids. The homology of CIP8 to TGRING1 is highest in the C-terminal part, but extends beyond the RING-H2 domain (FIG. 1A). Further database research revealed that, although many sequences from every eukaryotic phylum contain the RING-H2 domain, some contain a RING-H2 domain with a conserved motif consisting of 25-40 amino acids directly N-terminal to the RING-H2 domain. These extended RING-H2 domains are found in sequences from plant, animal and viral origin (FIG. 1B).

TGRING1 Expression

The expression level of TGRING1 in bottom internodes is higher during the low temperature treatment compared to the control treatment (FIG. 2A). It is higher in the earlier part of the treatment than in later stages of the treatment. TGRING1 expression was examined in different tissues after planting of the bulbs. Expression in the internodes is examined at the moment when they just start to elongate rapidly and expression in the flower when it shows the first colouring. Roots and leaves show no rapid growth phase, so expression is examined at an arbitrary moment (FIG. 2B). The highest expression is detected in flower tissue and the lowest in the leaves.

We showed that one of the underlying mechanisms of low temperature induced stem elongation in tulips is a gradual change in the sensitivity for auxin in the bottom internodes over the course a low temperature treatment of a few months. This was shown by an increase in auxin induced internodal elongation and auxin induced gene expression of primary auxin response genes, after longer periods of low temperature treatment. By using differential display we have isolated a cDNA clone that is expressed at higher levels during the low temperature treatment, as compared to a control treatment. It codes for a protein with a C-terminal RING-H2 domain.

Although this is a feature shared by a lot of proteins, both in arabidopsis and other species, only two arabidopsis sequences showed homology over the whole length of TGRING1. One of these, AIP2, has a sufficiently high homology to be a true homologue. This is also true for rice OSRING1, which has slightly higher identity and similarity because it is of monocotyledonous origin, as TGRING1. The Arabidopsis CIP8 is a more distantly related protein. The extended RING-H2 domain shared by these four proteins is conserved beyond the plant kingdom, which indicates a special function for this domain.

The Arabidopsis proteins AIP2 and CIP8 are isolated as proteins interacting with developmental regulators. CIP8 interacts with COP1 through specific interaction of the RING-H2 domain of CIP8 and the RING-finger domain of COP1 [13]. The interaction of AIP2 with ABI3 is mediated by the C-terminal half of AIP2, containing the RING-H2 domain [8]. But surprisingly, it interacts with the B2 and B3 domains of ABI3, which do not contain a RING-finger domain. So either the C-terminal part of AIP2 that does not contain the RING-H2 domain interacts with ABI3, or the RING-H2 domains can interact with different domains with no apparent sequence homology, despite the fact that the RING-H2 domains are highly similar in sequence (43% identity and 71% similarity between the RING-H2 domains of AIP2 and CIP8).

Low temperature induced stem elongation can be viewed as a form of dormancy breaking. Stratification, vernalisation and dormancy breaking in tree buds are similar processes driven by low temperature. Interesting now is that the TGRING1 arabidopsis homologue AIP2 is an ABI3 interacting factor. The Arabidopsis abscisic acid-insensitive3 (abi3) mutant was originally isolated for its ability to germinate in the presence of inhibiting concentrations of abscisic acid (ABA; [7]) and has a role in embryo maturation and dormancy maintenance [9]. Recent publications have shown that ABI3 also has a role in vegetative quiescence processes. The abi3-4 mutant shows a rapid induction of flowering and ABI3 is expressed in the apex of dark grown seedlings [8;11;12]. Another recent publication proposes a function for the RING finger domain in targeted ubiquitin-mediated proteolysis. RING finger proteins act therein as E3 ubiquitin protein ligases [6].

Taken all these things together we show here that the low temperature induced TGRING1 expression has a role in targeting the tulip homologue of ABI3 for proteolysis, and thereby removing the state of dormancy, allowing the plant to grow under favourable conditions. Analysis of AIP2 in Arabidopsis during processes as stratification and vernalization and its influence on ABI3 protein levels are ways to further show this phenomenon, considering that the fact remains that two totally different approaches to analyze similar phenomena as seed dormancy and low temperature induced flowering in tulip result in the cloning of homologous proteins having the above described RING-H2 motif.

The expression of AIP2 during cold stratification.

Purpose of the Experiment

Determine the expression pattern of the arabidopsis homologue AIP2 of the cloned tulip TGRING1 during seed stratification by low temperature.

Experimental Setup

Dry *Arabidopsis thaliana* seeds of the Cape Verdian ecotype (Cvi, planting date 21 june, harvested november 1, start experiment november 11, all in 2001) were sown on wet filter paper and either put in the dark at 20° C. or at 4° C. for 1, 3, 5 or 7 days. Per treatment, a part of the seeds was after treatment transferred to 20° C. in the light (16 hrs light/8 hrs dark) to determine germination percentage; the rest of the seeds were frozen in liquid nitrogen and stored at −80° C. for RNA isolation. Germination percentage was determined 7 days after seeds were placed at 20° in the light. RNA extraction and Northernblotting was performed as described for the experiments on tulip.

Results

FIGS. 4a and b show the expression level of AIP2 after the indicated amount of days of treatment. The AIP2 probe hybridized with a single band of approximately 1200 bp. The expression level is strongly increased 1 day after incubation at 4° C., both compared to dry seeds (twelvefold higher) and seeds incubated at 20° C. (fivefold higher). The expression stays higher during the low temperature treatment, compared to the 20° C. treatment.

FIG. 3c shows the germination percentage of the seeds after the different treatments. The seeds were not very dormant, yet the low temperature treatment increased the germination percentage, compared to seeds kept at 20° C. Germination was 100% after three or more days at 4° C. The results show that the arabidopsis AIP2 mRNA is strongly upregulated during cold stratification. This shows that the AIP2 protein is not only conserved in sequence but also in function, moreover it is even functionally conserved in different developmental processes requiring low temperature induction, namely low temperature induced stem elongation in tulip and seed stratification in arabidopsis. The increased expression during cold stratification correlates with an increased germination percentage after the treatment. Because AIP2 interacts with ABI3 and has a RING-H2 domain it is likely that the dormancy breaking occurs by proteolytic targeting of the ABI3 protein via ubiquitination, thus removing the state of dormancy. AIP2 would then act as a monomeric E3 ubiquitin ligase. By analogy the tulip TGRING1 protein would have the same function in the process of low temperature induction of stem elongation, which can be seen as a form of dormancy breaking. This experiment shows that AIP2 and homologous proteins are clear markers for dormancy breaking. It also shows the involvement of a RING domain protein in dormancy breaking in another process as low temperature induced stem elongation in tulips, namely cold seed stratification.

FIGURE LEGENDS

FIG. 1A Multiple alignment of TGRING1 and homologous proteins from Arabidopsis and rice. Residues are shaded black when more than 50% of the residues is identical and gray when more than 50% of the residues is similar. Fully conserved residues are indicated by an asterisk, conserved substitutions by a colon, and semi conserved substitutions by a dot. The RING-H2 domain is underlined, and the N-terminal extension of the RING-H2 domain is underlined by a dashed line.

FIG. 1B Multiple alignment of the extended RING-H2 domains of proteins from animal, plant and viral origin. Shading is as indicated for A. Species are indicated as follows: Mm is *Mus Musculus* (mouse), Rr is *Rattus rattus* (rat), At is *Arabidopsis thaliana*, Os is *Oryza sativa* (rice), Hs is *Homo sapiens* (human), Tg is *Tulipa gesneriana* and Hh is human Herpesvirus. Database accession numbers are: PRAJA1 NP_032879, NDAP1 BAA06979, RHC2a AAC69860, os329 BAA88184, hs311 BAA91254 and ICPO P28284.

FIG. 2A Expression of TGRING-1 in the bottom internode of tulip during low temperature treatment (5° C.) compared to a control treatment (17° C.).

FIG. 2B Expression of TGRING-1 in different tissues after planting. As a reference, the expression level in the bottom internode at day 0 after planting is shown. This expression level is the same as that at week 12 of the 5° C. treatment in FIG. 2A (different exposure times are used for FIG. 2A and FIG. 2B). The other internode samples were taken at the moment that they started to grow rapidly: leaves and roots show no exponential growth phase and samples were taken at an arbitrary moment; flower tissue was sampled when colouring started. 25 micrograms of total RNA was used per lane. Equal loading was checked by ethidium bromide staining (not shown).

FIG. 3

Nucleic acid of TGRING1 (SEQ. ID. NO: 14)

The predicted 327 amino acid (SEQ. ID. NO: 15)open reading frame is coded for by bases 104-1182 and is indicated above the nucleic acid sequence. The bases coding for the RING-H2 domain are underlined.

FIG. 4A

Expression of AIP2 during treatment of imbibed seeds at either 4° C. or 20° C. An RNA probe was used complementary to bp 665-1120 of the AIP2 mRNA sequence (GenBank accesion ATH251087). The band corresponds to a size of approximately 1200 bp. 8 μg of total RNA was loaded per lane; the bottom panel shows a methylene blue staining of the blot to confirm equal loading. ds indicates dry seeds.

FIG. 4B

Quantification of the intensities of the bands in FIG. 4a.

FIG. 4C

Percentage germination of the seeds after the indicated treatments.

INCORPORATION OF SEQUENCE LISTING

Incorporated herein by reference in its entirety is the Sequence Listing for the application. The Sequence Listing is disclosed on a computer-readable ASCII text file titled, "sequence.txt", created on Dec. 15, 2008. The sequence.txt file is 25 kb in size.

Literature

REFERENCE LIST

1. Ausubel, F, Brent, R, Kingston, R E, Moore, D D, Seidman, J G, Smith, J A, Struhl, K: Short protocols in molecular biology. John Wiley & Sons, New York (1995).
2. Bauer, D, Muller, H, Reich, J, Riedel, H, Ahrenkiel, V, Warthoe, P, Strauss, M: Identification of differentially expressed mRNA species by an improved display technique (DDRT-PCR). Nucleic Acids Res. 21: 4272-4280 (1993)
3. Chang, S, Puryear, J, Cairney, J: A simple and efficient method for isolating RNA from pine trees. Plant Molecular Biology Reporter 11: 114-117 (1993).
4. De Hertogh, A A, Le Nard, M: Tulipa. In: De Hertogh, A. A and Le Nard, M. (eds), The Physiology of Flower Bulbs, pp. 617-682. Elsevier Science Publishers; Amsterdam (1993).
5. Dennis, F G Jr: A physiological comparison of seed and bud dormancy. In: Lang, G, A. (ed), Plant Dormancy: Phsysiology, Biochemistry and Molecular Biology, pp. 47-56. CAB International, Wallingford UK (1996).
6. Freemont, P S: RING for destruction? [In Process Citation]. Curr. Biol. 10: R84-R87 (2000).
7. Koornneef, M, Reuling, G, Karssen, C M: The isolation and characterization of abscisic acid-insensitive mutants of Arabidopsis thaliana. Physiologia Plantarum 61: 377-383 (1984).
8. Kurup, S, Jones, H D, Holdsworth, M J: Interactions of the developmental regulator ABI3 with proteins identified from developing Arabidopsis seeds. Plant J 21: 143-155 (2000).
9. Ooms, J J J, Lèon-Kloosterziel, K M, Bartels, D, Koornneef, M, Karssen, C M: Acquisition of desiccation tolerance and longevity in seeds of Arabodopsis thaliana. A comparative study using abscicic acid-insensitive abi3 mutants. Plant Physiol 102: 1185-1191 (1993).
10. Rietveld, P L, Wilkinson, C, Fransen, H M, Balk, P A, Van der Plas, L H W, Weisbeek, P J, De Boer, A D: Low temperature sensing in tulip is mediated through an increased response to auxin. J Exp Bot 51: (2000).
11. Rohde, A, De Rycke, R, Beeckman, T, Engler, G, Van Montagu, M, Boerjan, W: ABI3 affects plastid differentiation in dark-grown arabidopsis seedlings [In Process Citation]. Plant Cell 12: 35-52 (2000).
12. Rohde, A, Montagu, Mv, Boerjan, W: The ABSCICIC ACID-INSENSITIVE3 (ABI3) gene is expressed during vegetative quiescence processes in Arabidopsis. Plant, Cell and Environment 216-270 (1999).
13. Torii, K U, Stoop-Myer, C D, Okamoto, H, Coleman, J E, Matsui, M, Deng, X W: The RING finger motif of photomorphogenic repressor COP1 specifically interacts with the RING-H2 motif of a novel Arabidopsis protein. J Biol Chem 274: 27674-27681 (1999).
14. pBIN19 Nucleic Acids Research 12(22), 8711-8721 (1984).
15. Bachmair, A, Novatchkova, M, Potuschak, T, Eisenhaber, F: Ubiquitylation in plants: a post-genomic look at a post-translational modification. Trends Plant Sci 2001, 6:463-70.
16. Kurup, S. Jones, H D, Holdsworth, M J: Interactions of the developmental regulator ABI3 with proteins identified from developing Arabidopsis seeds. Plant J 2000, 21:143-55.
17. Stoop-Myer, C, Torii, K U, McNellis, T W, Coleman, J E, Deng, X W: Short communication: the N-terminal fragment of Arabidopsis photomorphogenic repressor COP1 maintains partial function and acts in a concentration-dependent manner. Plant J 1999, 20:713-7.
18. McNellis, T W, Torii, K U, Deng, X W: Expression of an N-terminal fragment of COP1 confers a dominant-negative effect on light-regulated seedling development in Arabidopsis. Plant Cell 1996, 8:1491-503.
19. McNellis, T W, Von Arnim, A G, Deng, X W: Overexpression of Arabidopsis COP1 results in partial suppression of light-mediated development: evidence for a light-inactivable repressor of photomorphogenesis. Plant Cell 1994, 6:1391-400.
20. Freemont, P S: RING for destruction? Curr Biol 2000, 10: R84-7.
21. Potuschak, T. Stary, S, Schlogelhofer, P, Becker, F, Nejinskaia, V, Bachmair, A: PRT1 of Arabidopsis thaliana encodes a component of the plant N-end rule pathway. Proc Natl Acad Sci USA 1998, 95:7904-8.
22. Tamminen, I, Makela, P, Heino, P, Palva, ET: Ectopic expression of ABI3 gene enhances freezing tolerance in response to abscisic acid and low temperature in Arabidopsis thaliana. Plant J 2001, 25:1-8.
23. Torii, K U, Stoop-Myer, C D, Okamoto, H, Coleman, J E, Matsui, M, Deng, X W: The RING finger motif of photomorphogenic repressor COP1 specifically interacts with the RING-H2 motif of a novel Arabidopsis protein. J Biol Chem 1999, 274:27674-81.

The invention claimed is:

1. An isolated and/or recombinant nucleic acid encoding a plant RING-H2 protein or functional fragment thereof comprising a motif having an amino acid sequence that is at least 95% identical to amino acid residues 248-288 as shown in SEQ. ID. NO. 15, wherein the protein or functional fragment thereof binds to and catalyzes ubiquitination and/or proteolysis of a developmental regulatory protein, wherein said developmental regulatory protein is COP1.

2. The nucleic acid according to claim 1 wherein said plant comprises a bulb.

3. A vector comprising the nucleic acid according to claim 1.

4. An isolated host cell comprising the nucleic acid according to claim 1.

5. A vector comprising the nucleic acid according to claim 2.

6. An isolated host cell comprising the nucleic acid according to claim 2.

7. An isolated host cell comprising the vector according to claim 3.

8. The nucleic acid according to claim 1, wherein said amino acid sequence has one or two amino acid substitutions at a position selected from the group consisting of position 250, 254, 256, 259, and 269 as compared to the amino acid sequence of SEQ ID NO: 15.

9. An isolated and/or recombinant nucleic acid encoding a plant RING-H2 protein or functional fragment thereof, comprising a nucleic acid sequence that is at least 95% identical to SEQ ID NO:14, wherein the protein or functional fragment thereof binds to and catalyzes ubiquitination and/or proteolysis of a developmental regulatory protein, wherein said developmental regulatory protein is COP1 and/or abscisic acid-insensitive3 (ABI3).

* * * * *